(12) United States Patent
Finlay et al.

(10) Patent No.: US 9,220,887 B2
(45) Date of Patent: Dec. 29, 2015

(54) ELECTRODE LEAD INCLUDING A DEPLOYABLE TISSUE ANCHOR

(75) Inventors: Matthew S. Finlay, Minneapolis, MN (US); William J. Rissmann, Deephaven, MN (US)

(73) Assignee: Astora Women's Health LLC, Eden Prairie, MN (US)

( * ) Notice: Subject to any disclaimer, the term of this patent is extended or adjusted under 35 U.S.C. 154(b) by 345 days.

(21) Appl. No.: 13/490,600

(22) Filed: Jun. 7, 2012

(65) Prior Publication Data

US 2012/0316627 A1 Dec. 13, 2012

Related U.S. Application Data

(60) Provisional application No. 61/494,950, filed on Jun. 9, 2011.

(51) Int. Cl.
*A61N 1/05* (2006.01)

(52) U.S. Cl.
CPC .............. *A61N 1/0514* (2013.01); *A61N 1/057* (2013.01); *A61N 1/059* (2013.01); *A61N 1/0512* (2013.01); *A61N 1/0558* (2013.01); *A61N 2001/058* (2013.01)

(58) Field of Classification Search
CPC ..... A61N 1/05; A61N 1/0558; A61N 1/0551; A61N 1/057; A61N 1/058; A61N 1/059; A61N 1/0592; A61M 5/14276; A61M 5/00
USPC ......... 607/115, 116, 117, 119, 122, 126, 129, 607/130
See application file for complete search history.

(56) References Cited

U.S. PATENT DOCUMENTS

| 3,628,538 | A | 12/1971 | Vincent et al. |
| 3,640,284 | A | 2/1972 | De Langis |
| 3,646,940 | A | 3/1972 | Timm et al. |

(Continued)

FOREIGN PATENT DOCUMENTS

| DE | 8506522.6 U1 | 4/1985 |
| EP | 0245547 | 11/1987 |

(Continued)

OTHER PUBLICATIONS

Pietrafitta, Joseph J., MD, "Laser Therapy of Cancer of the Gastrointestinal and Biliary Tracts", Seminars in Surgical Oncology 5:17-29, 1989.

(Continued)

*Primary Examiner* — Christopher D Koharski
*Assistant Examiner* — Pamela M Bays
(74) *Attorney, Agent, or Firm* — Westman, Champlin & Koehler, P.A.

(57) ABSTRACT

An electrode lead comprises a tubular lead body, an electrode supported by the lead body, a rotatable member, a deployable member and a deployment mechanism. The rotatable member is contained within a distal end of the tubular lead body. The deployable member is attached to the rotatable member and comprises a tissue anchor. The deployment mechanism is configured to drive the deployable member along a central axis and out the distal end of the tubular lead body responsive to rotation of the rotatable member about the central axis. In one embodiment, the deployable member does not rotate about the central axis with the rotation of the rotatable member.

13 Claims, 5 Drawing Sheets

(56) References Cited

U.S. PATENT DOCUMENTS

| | | |
|---|---|---|
| 3,650,276 A | 3/1972 | Burghele et al. |
| 3,662,758 A | 5/1972 | Glover |
| 3,667,477 A | 6/1972 | Susset et al. |
| 3,866,613 A | 2/1975 | Kenny et al. |
| 3,870,051 A | 3/1975 | Brindley |
| 3,926,178 A | 12/1975 | Feldzamen |
| 3,941,136 A | 3/1976 | Bucalo |
| 3,983,865 A | 10/1976 | Shepard |
| 3,983,881 A | 10/1976 | Wickham |
| 3,999,555 A | 12/1976 | Person |
| 4,010,758 A | 3/1977 | Rockland et al. |
| 4,023,574 A | 5/1977 | Nemec |
| 4,030,509 A | 6/1977 | Heilman et al. |
| 4,044,774 A | 8/1977 | Corbin et al. |
| 4,106,511 A | 8/1978 | Erlandsson |
| 4,136,684 A | 1/1979 | Scattergood et al. |
| 4,139,006 A | 2/1979 | Corey |
| 4,153,059 A | 5/1979 | Fravel et al. |
| 4,157,087 A | 6/1979 | Miller et al. |
| 4,165,750 A | 8/1979 | Aleev et al. |
| 4,177,819 A | 12/1979 | Kofsky et al. |
| 4,217,913 A | 8/1980 | Dutcher |
| 4,222,377 A | 9/1980 | Burton |
| 4,257,428 A * | 3/1981 | Barton et al. ............... 607/128 |
| 4,290,420 A | 9/1981 | Manetta |
| 4,387,719 A | 6/1983 | Plevnik et al. |
| 4,402,328 A | 9/1983 | Doring |
| 4,406,288 A | 9/1983 | Horwinski et al. |
| 4,414,986 A | 11/1983 | Dickhudt et al. |
| 4,431,001 A | 2/1984 | Hakansson et al. |
| 4,457,299 A | 7/1984 | Cornwell |
| 4,492,233 A | 1/1985 | Petrofsky et al. |
| 4,515,167 A | 5/1985 | Hochman |
| 4,542,753 A | 9/1985 | Brenman et al. |
| 4,550,737 A | 11/1985 | Osypka |
| 4,568,339 A | 2/1986 | Steer |
| 4,569,351 A | 2/1986 | Tang |
| 4,571,749 A | 2/1986 | Fischell |
| 4,580,578 A | 4/1986 | Barsom |
| 4,585,005 A | 4/1986 | Lue et al. |
| 4,590,949 A | 5/1986 | Pohndorf |
| 4,602,624 A | 7/1986 | Naples et al. |
| 4,607,639 A | 8/1986 | Tanagho et al. |
| 4,628,942 A | 12/1986 | Sweeney et al. |
| 4,688,575 A | 8/1987 | DuVall |
| 4,703,755 A | 11/1987 | Tanagho et al. |
| 4,731,083 A | 3/1988 | Fischell |
| 4,739,764 A | 4/1988 | Lue et al. |
| 4,750,494 A | 6/1988 | King |
| 4,771,779 A | 9/1988 | Tanagho et al. |
| 4,785,828 A | 11/1988 | Maurer |
| 4,881,526 A | 11/1989 | Johnson et al. |
| 4,913,164 A | 4/1990 | Greene et al. |
| 4,941,874 A | 7/1990 | Sandow et al. |
| 5,013,292 A | 5/1991 | Lemay |
| 5,019,032 A | 5/1991 | Robertson |
| 5,061,265 A | 10/1991 | Abela et al. |
| 5,074,632 A | 12/1991 | Potter |
| 5,082,006 A | 1/1992 | Jonasson |
| 5,094,242 A | 3/1992 | Gleason et al. |
| 5,102,402 A | 4/1992 | Dror et al. |
| 5,103,835 A | 4/1992 | Yamada et al. |
| 5,112,344 A | 5/1992 | Petros |
| 5,125,925 A | 6/1992 | Lundahl |
| 5,193,539 A | 3/1993 | Schulman et al. |
| 5,193,540 A | 3/1993 | Schulman et al. |
| 5,199,430 A | 4/1993 | Fang et al. |
| 5,269,777 A | 12/1993 | Doiron et al. |
| 5,285,781 A | 2/1994 | Brodard |
| 5,291,902 A | 3/1994 | Carman |
| 5,312,439 A | 5/1994 | Loeb |
| 5,324,316 A | 6/1994 | Schulman et al. |
| 5,324,324 A | 6/1994 | Vachon et al. |
| 5,330,507 A | 7/1994 | Schwartz |
| 5,344,439 A | 9/1994 | Otten |
| 5,358,514 A | 10/1994 | Schulman et al. |
| 5,405,367 A | 4/1995 | Schulman et al. |
| 5,411,016 A | 5/1995 | Kume et al. |
| 5,411,548 A | 5/1995 | Carman |
| 5,417,226 A | 5/1995 | Juma |
| 5,423,329 A | 6/1995 | Ergas |
| 5,428,699 A | 6/1995 | Pon |
| 5,431,647 A | 7/1995 | Purcell, Jr. et al. |
| 5,452,719 A | 9/1995 | Eisman et al. |
| 5,458,595 A | 10/1995 | Tadir et al. |
| 5,484,445 A | 1/1996 | Knuth |
| 5,518,504 A | 5/1996 | Polyak |
| 5,520,606 A | 5/1996 | Schoolman et al. |
| 5,530,780 A | 6/1996 | Ohsawa |
| 5,533,508 A | 7/1996 | Doiron |
| 5,562,717 A | 10/1996 | Tippey et al. |
| 5,569,240 A | 10/1996 | Dowlatshahi et al. |
| 5,569,351 A | 10/1996 | Menta et al. |
| 5,571,148 A | 11/1996 | Loeb et al. |
| 5,593,405 A | 1/1997 | Osypka |
| 5,611,515 A | 3/1997 | Benderev et al. |
| 5,611,768 A | 3/1997 | Tutrone, Jr. |
| 5,634,462 A | 6/1997 | Tyler et al. |
| 5,645,562 A | 7/1997 | Haan et al. |
| 5,658,327 A * | 8/1997 | Altman et al. ............... 607/127 |
| 5,695,583 A | 12/1997 | van den Bergh et al. |
| 5,702,428 A | 12/1997 | Tippey et al. |
| 5,728,092 A | 3/1998 | Doiron et al. |
| 5,730,700 A | 3/1998 | Walther et al. |
| 5,733,277 A | 3/1998 | Pallarito |
| 5,752,978 A | 5/1998 | Chancellor |
| 5,807,390 A | 9/1998 | Fuller et al. |
| 5,807,397 A | 9/1998 | Barreras |
| 5,824,005 A | 10/1998 | Motamedi et al. |
| 5,824,027 A | 10/1998 | Hoffer et al. |
| 5,833,595 A | 11/1998 | Lin |
| 5,842,478 A | 12/1998 | Benderev et al. |
| 5,854,422 A | 12/1998 | McKeon et al. |
| 5,860,425 A | 1/1999 | Benderev et al. |
| 5,876,426 A | 3/1999 | Kume et al. |
| 5,891,082 A | 4/1999 | Leone et al. |
| 5,891,136 A | 4/1999 | McGee et al. |
| 5,899,909 A | 5/1999 | Claren et al. |
| 5,911,720 A | 6/1999 | Bourne et al. |
| 5,927,282 A | 7/1999 | Lenker et al. |
| 5,931,864 A | 8/1999 | Chastain et al. |
| 5,947,958 A | 9/1999 | Woodard et al. |
| 5,954,761 A | 9/1999 | Machek et al. |
| 5,957,920 A | 9/1999 | Baker |
| 5,957,965 A | 9/1999 | Moumane et al. |
| 5,978,712 A | 11/1999 | Suda et al. |
| 5,984,854 A | 11/1999 | Ishikawa et al. |
| 5,997,571 A | 12/1999 | Farr et al. |
| 6,002,964 A | 12/1999 | Feler et al. |
| 6,013,053 A | 1/2000 | Bower et al. |
| 6,026,326 A | 2/2000 | Bardy |
| 6,027,456 A | 2/2000 | Feler et al. |
| 6,027,524 A | 2/2000 | Petit |
| 6,039,686 A | 3/2000 | Kovac |
| 6,042,534 A | 3/2000 | Gellman et al. |
| 6,051,017 A | 4/2000 | Loeb et al. |
| 6,055,456 A | 4/2000 | Gerber |
| 6,061,596 A | 5/2000 | Richmond et al. |
| 6,086,558 A | 7/2000 | Bower et al. |
| 6,096,030 A | 8/2000 | Ortiz |
| 6,104,955 A | 8/2000 | Bourgeois |
| 6,104,960 A | 8/2000 | Duysens et al. |
| 6,110,101 A | 8/2000 | Tihon et al. |
| 6,131,575 A | 10/2000 | Lenker et al. |
| 6,135,945 A | 10/2000 | Sultan |
| 6,141,594 A | 10/2000 | Flynn et al. |
| 6,146,409 A | 11/2000 | Overholt et al. |
| 6,161,029 A | 12/2000 | Spreigl et al. |
| 6,178,356 B1 | 1/2001 | Chastain et al. |
| 6,185,452 B1 | 2/2001 | Schulman et al. |
| 6,208,894 B1 | 3/2001 | Schulman et al. |
| 6,240,315 B1 | 5/2001 | Mo et al. |
| 6,240,316 B1 | 5/2001 | Richmond et al. |
| 6,243,607 B1 | 6/2001 | Mintchev et al. |

(56) References Cited

U.S. PATENT DOCUMENTS

| | | |
|---|---|---|
| 6,266,557 B1 | 7/2001 | Roe et al. |
| 6,266,564 B1 | 7/2001 | Hill et al. |
| 6,270,492 B1 | 8/2001 | Sinofsky |
| 6,304,786 B1 | 10/2001 | Heil et al. |
| 6,328,686 B1 | 12/2001 | Kovac |
| 6,341,236 B1 | 1/2002 | Osorio et al. |
| 6,354,991 B1 | 3/2002 | Gross et al. |
| 6,360,750 B1 | 3/2002 | Gerber et al. |
| 6,366,814 B1 | 4/2002 | Boveja et al. |
| 6,382,214 B1 | 5/2002 | Raz et al. |
| 6,391,052 B2 | 5/2002 | Buirge et al. |
| 6,397,109 B1 | 5/2002 | Cammilli et al. |
| 6,398,778 B1 | 6/2002 | Gu et al. |
| 6,407,308 B1 | 6/2002 | Roe et al. |
| 6,418,930 B1 | 7/2002 | Fowler |
| 6,423,055 B1 | 7/2002 | Farr et al. |
| 6,482,197 B2 | 11/2002 | Finch et al. |
| 6,505,082 B1 | 1/2003 | Scheiner et al. |
| 6,522,806 B1 | 2/2003 | James, IV et al. |
| 6,524,274 B1 | 2/2003 | Rosenthal et al. |
| 6,572,609 B1 | 6/2003 | Farr et al. |
| 6,582,441 B1 | 6/2003 | He et al. |
| 6,600,956 B2 | 7/2003 | Maschino et al. |
| 6,612,977 B2 | 9/2003 | Staskin et al. |
| 6,616,653 B2 | 9/2003 | Beyar et al. |
| 6,626,900 B1 | 9/2003 | Sinofsky et al. |
| 6,641,524 B2 | 11/2003 | Kovac |
| 6,650,943 B1 | 11/2003 | Whitehurst et al. |
| 6,652,449 B1 | 11/2003 | Gross et al. |
| 6,652,450 B2 | 11/2003 | Neisz et al. |
| 6,658,297 B2 | 12/2003 | Loeb |
| 6,659,936 B1 | 12/2003 | Furness et al. |
| 6,706,004 B2 | 3/2004 | Tearney et al. |
| 6,708,056 B2 | 3/2004 | Duchon et al. |
| 6,712,772 B2 | 3/2004 | Cohen et al. |
| 6,735,474 B1 | 5/2004 | Loeb et al. |
| 6,745,079 B2 | 6/2004 | King |
| 6,796,972 B1 | 9/2004 | Sinofsky et al. |
| 6,802,807 B2 | 10/2004 | Anderson et al. |
| 6,829,411 B2 | 12/2004 | Easley |
| 6,862,480 B2 | 3/2005 | Cohen et al. |
| 6,896,651 B2 | 5/2005 | Gross et al. |
| 6,899,706 B2 | 5/2005 | Slatkine |
| 6,911,003 B2 | 6/2005 | Anderson et al. |
| 6,941,171 B2 | 9/2005 | Mann et al. |
| 6,952,613 B2 | 10/2005 | Swoyer et al. |
| 6,953,457 B2 | 10/2005 | Farr et al. |
| 6,964,643 B2 | 11/2005 | Hovland et al. |
| 6,964,699 B1 | 11/2005 | Carns et al. |
| 6,971,393 B1 | 12/2005 | Mamo et al. |
| 6,986,764 B2 | 1/2006 | Davenport et al. |
| 7,079,882 B1 | 7/2006 | Schmidt |
| 7,112,195 B2 | 9/2006 | Boll et al. |
| 7,120,499 B2 | 10/2006 | Thrope et al. |
| 7,131,963 B1 | 11/2006 | Hyde |
| 7,135,034 B2 | 11/2006 | Friedman et al. |
| 7,169,140 B1 | 1/2007 | Kume |
| 7,207,984 B2 | 4/2007 | Farr et al. |
| 7,261,730 B2 | 8/2007 | Friedman et al. |
| 7,319,905 B1 | 1/2008 | Morgan et al. |
| 7,328,068 B2 | 2/2008 | Spinelli et al. |
| 7,330,764 B2 | 2/2008 | Swoyer et al. |
| 7,343,202 B2 | 3/2008 | Mrva et al. |
| 7,357,796 B2 | 4/2008 | Farr et al. |
| 7,376,467 B2 | 5/2008 | Thrope et al. |
| 7,376,468 B2 | 5/2008 | King et al. |
| 7,449,026 B2 | 11/2008 | Zalesky et al. |
| 7,613,516 B2 | 11/2008 | Cohen et al. |
| 7,628,795 B2 | 12/2009 | Karwoski et al. |
| 7,647,113 B2 | 1/2010 | Wirbisky et al. |
| 7,725,197 B2 | 5/2010 | Soltis et al. |
| 7,771,345 B1 | 8/2010 | O'Donnell |
| 8,019,443 B2 | 9/2011 | Schleicher et al. |
| 8,052,731 B2 | 11/2011 | Soltis et al. |
| 8,160,710 B2 | 4/2012 | Buysman et al. |
| 8,195,296 B2 | 6/2012 | Longhini et al. |
| 2001/0002441 A1 | 5/2001 | Boveja |
| 2001/0003799 A1 | 6/2001 | Boveja |
| 2001/0018549 A1 | 8/2001 | Scetbon |
| 2002/0055761 A1 | 5/2002 | Mann et al. |
| 2002/0103521 A1* | 8/2002 | Swoyer et al. ................ 607/116 |
| 2002/0151948 A1* | 10/2002 | King et al. ..................... 607/122 |
| 2002/0161382 A1 | 10/2002 | Neisz et al. |
| 2002/0165566 A1 | 11/2002 | Ulmsten |
| 2003/0018365 A1 | 1/2003 | Loeb |
| 2003/0023296 A1 | 1/2003 | Osypka |
| 2003/0028232 A1 | 2/2003 | Camps et al. |
| 2003/0060868 A1 | 3/2003 | Janke et al. |
| 2003/0100930 A1 | 5/2003 | Cohen et al. |
| 2003/0171644 A1 | 9/2003 | Anderson et al. |
| 2003/0199961 A1 | 10/2003 | Bjorklund et al. |
| 2003/0236557 A1 | 12/2003 | Whitehurst et al. |
| 2003/0236558 A1 | 12/2003 | Whitehurst et al. |
| 2004/0015204 A1 | 1/2004 | Whitehurst et al. |
| 2004/0015205 A1 | 1/2004 | Whitehurst et al. |
| 2004/0039453 A1 | 2/2004 | Anderson et al. |
| 2004/0059392 A1 | 3/2004 | Parramon et al. |
| 2004/0068203 A1 | 4/2004 | Gellman et al. |
| 2004/0093053 A1 | 5/2004 | Gerber et al. |
| 2004/0133254 A1 | 7/2004 | Sterzer et al. |
| 2004/0186543 A1 | 9/2004 | King et al. |
| 2004/0242956 A1 | 12/2004 | Scorvo |
| 2004/0248979 A1 | 12/2004 | Brettman et al. |
| 2005/0038489 A1 | 2/2005 | Grill |
| 2005/0043580 A1 | 2/2005 | Watschke et al. |
| 2005/0065395 A1 | 3/2005 | Mellier |
| 2005/0113877 A1 | 5/2005 | Spinelli et al. |
| 2005/0119710 A1 | 6/2005 | Furness et al. |
| 2005/0143618 A1 | 6/2005 | Anderson et al. |
| 2005/0149156 A1 | 7/2005 | Libbus et al. |
| 2005/0216069 A1 | 9/2005 | Cohen et al. |
| 2005/0228346 A1 | 10/2005 | Goode et al. |
| 2005/0245787 A1 | 11/2005 | Cox et al. |
| 2005/0245874 A1 | 11/2005 | Carrez et al. |
| 2005/0250977 A1 | 11/2005 | Montpetit et al. |
| 2005/0255039 A1 | 11/2005 | Desai |
| 2006/0004421 A1 | 1/2006 | Bennett et al. |
| 2006/0004429 A1 | 1/2006 | Mrva et al. |
| 2006/0149345 A1 | 7/2006 | Boggs, II et al. |
| 2006/0241733 A1 | 10/2006 | Zhang et al. |
| 2006/0287571 A1 | 12/2006 | Gozzi et al. |
| 2007/0021650 A1 | 1/2007 | Rocheleau et al. |
| 2007/0043416 A1 | 2/2007 | Callas et al. |
| 2007/0050003 A1* | 3/2007 | Zarembo et al. ............... 607/116 |
| 2007/0100411 A1 | 5/2007 | Bonde |
| 2007/0123952 A1 | 5/2007 | Strother et al. |
| 2007/0179559 A1 | 8/2007 | Giftakis et al. |
| 2007/0185541 A1 | 8/2007 | DiUbaldi et al. |
| 2007/0239224 A1 | 10/2007 | Bennett et al. |
| 2007/0253997 A1 | 11/2007 | Giftakis et al. |
| 2007/0253998 A1 | 11/2007 | Giftakis et al. |
| 2007/0255333 A1 | 11/2007 | Giftakis et al. |
| 2007/0255341 A1 | 11/2007 | Giftakis et al. |
| 2007/0260288 A1 | 11/2007 | Gross |
| 2007/0265675 A1 | 11/2007 | Lund et al. |
| 2008/0009914 A1 | 1/2008 | Buysman et al. |
| 2008/0039828 A1 | 2/2008 | Jimenez et al. |
| 2008/0071321 A1 | 3/2008 | Boggs, II et al. |
| 2008/0132969 A1 | 6/2008 | Bennett et al. |
| 2008/0183254 A1* | 7/2008 | Bly et al. ....................... 607/116 |
| 2009/0012592 A1 | 1/2009 | Buysman et al. |
| 2009/0043356 A1 | 2/2009 | Longhini et al. |
| 2009/0157091 A1 | 6/2009 | Buysman |
| 2009/0259280 A1 | 10/2009 | Wilkin et al. |
| 2010/0049289 A1 | 2/2010 | Lund et al. |
| 2010/0076254 A1 | 3/2010 | Jimenez et al. |
| 2010/0274338 A1 | 10/2010 | Ollivier |
| 2010/0298757 A1 | 11/2010 | Frigstad |
| 2011/0301584 A1 | 12/2011 | Beck et al. |
| 2012/0095478 A1 | 4/2012 | Wang et al. |
| 2012/0157981 A1 | 6/2012 | Evans et al. |

(56) References Cited

U.S. PATENT DOCUMENTS

FOREIGN PATENT DOCUMENTS

| | | |
|---|---|---|
| EP | 1119314 B1 | 8/2001 |
| EP | 1 661 600 A1 | 5/2006 |
| GB | 2309388 | 7/1997 |
| WO | 9012617 | 11/1990 |
| WO | 9604955 | 2/1996 |
| WO | 9632916 | 10/1996 |
| WO | 9817190 A2 | 4/1998 |
| WO | 0000082 A1 | 1/2000 |
| WO | 0019940 | 4/2000 |
| WO | 0239890 A2 | 5/2002 |
| WO | 02069781 | 9/2002 |
| WO | 02078592 | 10/2002 |
| WO | 03002192 | 1/2003 |
| WO | 2006047833 | 5/2006 |
| WO | 2007097994 A2 | 8/2007 |
| WO | 2007126632 A3 | 11/2007 |
| WO | 2007145913 A1 | 12/2007 |
| WO | 2010107751 A2 | 9/2010 |

OTHER PUBLICATIONS

European Search Report and Written Opinion of 06011641.5 dated Aug. 21, 2006.
International Search Report and Written Opinion of PCT/US2007/004474 filed on Feb. 22, 2007.
U.S. Appl. No. 60/779,219, filed Mar. 3, 2006.
International Search Report and Written Opinion of PCT/US2007/000112 filed Jan. 3, 2007.
U.S. Appl. No. 12/406,434, filed Mar. 18, 2009.
U.S. Appl. No. 61/160,765, filed Mar. 17, 2009.
U.S. Appl. No. 60/578,742, filed Jun. 10, 2004.
Caldwell, K.P.S. "Electrical Stimulation.", Sphincter Research Unit, Royal Devon and Exeter Hospital, Exeter (England), Urol. Int. 29: 225, 1974. (1 page).
Caldwell, K.P.S. "The Use of Electrical Stimulation in Urinary Retention and Incontinence [Abridged]." Section of Urology, vol. 61, pp. 35-39, Jul. 1968.
Caldwell, K.P.S. et al. "Urethral Pressure Recordings in Male Incontinents Under Electrical Stimulation." Investigative Urology vol. 5, No. 6, pp. 572-579, May 1968.
Caldwell, K.P.S. et al. "Stress Incontinence in Females: Report on 31 Cases Treated by Electrical Implant." J. Obstet. Gynaec. Brit. Cwlth vol. 75, pp. 777-780, Jul. 1968.
International Search Report and Written Opinion for PCT/US2011/023677 dated Apr. 21, 2011.
Notification of the First Office Action from Chinese patent application No. 200780007709.2, mailed Sep. 27, 2010.
Dietz et al., Mechanical Properties of Urogynecologic Implant Materials, Int. Urogynecol J. (2003) 14:239-243.
Iglesia et al., "The Use of Mesh in Gynecologic Surgery", Int. Urogynecol J. (1997) 8:105-115.
Partial European Search Report from European Patent Application No. 10176162.5, mailed Jan. 21, 2011.
Yamanishi et al., "Electrical Stimulation for Stress Incontinence", Int. Urogynecol J (1998) 9:281-290 Springer-Verlag London Ltd.
Yamamoto et al., "Optimal parameters for effective electrical stimulation of the anal sphincters in a child with fecal incontinence: preliminary report," Pediatr Surg Int (1993) 8:132-137.
Extended European Search Report and Search Opinion for European patent application No. EP 10176162.5 dated Apr. 28, 2011.
U.S. Appl. No. 13/431,594, filed Mar. 27, 2012.
U.S. Appl. No. 61/096,387, filed Sep. 12, 2008.
U.S. Appl. No. 60/948,908, filed Jul. 10, 2007.

\* cited by examiner

ELECTRODE LEAD INCLUDING A DEPLOYABLE TISSUE ANCHOR

CROSS-REFERENCE TO RELATED APPLICATIONS

The present application claims the benefit of U.S. provisional patent application Ser. No. 61/494,950 filed Jun. 9, 2011, the content of which is hereby incorporated by reference in its entirety.

FIELD OF THE INVENTION

Embodiments of the present invention generally relate to an anchor that facilitates securing devices or components to internal tissue of a patient and preventing migration of the devices or components from their intended location relative to the tissue of the patient.

BACKGROUND OF THE INVENTION

Implantable electronic stimulator devices, such as neuromuscular stimulation devices, have been disclosed for use in the treatment of various pelvic conditions, such as urinary incontinence, fecal incontinence and sexual dysfunction. Such devices generally include one or more electrodes that are coupled to a control unit by electrode leads. Electrical signals are applied to the desired pelvic tissue of the patient through the electrode leads in order to treat the condition of the patient. Exemplary implantable electronic stimulator devices and uses of the devices are disclosed in U.S. Pat. Nos. 6,354,991, 6,652,449, 6,712,772 and 6,862,480, each of which is hereby incorporated by reference in its entirety.

Electrical leads utilize anchors to secure the one or more electrodes in tissue of the patient. Exemplary anchors include helical coils and mesh, such as that disclosed in (A92.12-0136), which is incorporated herein by reference in its entirety. It is desirable, for example, that such anchors prevent relative movement between the anchor and the tissue in which the anchor in embedded, are easy to install in the tissue, avoid damaging the tissue during the implantation procedure, can be removed without significantly damaging the tissue, and/or have other features or benefits recognized by those skilled in the art.

SUMMARY

Embodiments of the invention are directed to an implantable electrode lead. In some embodiments, the electrode lead comprises a tubular lead body, an electrode supported by the lead body, a rotatable member, a deployable member and a deployment mechanism. The rotatable member is contained within a distal end of the tubular lead body. The deployable member is attached to the rotatable member and comprises a tissue anchor. The deployment mechanism is configured to drive the deployable member along a central axis and out the distal end of the tubular lead body responsive to rotation of the rotatable member about the central axis. In one embodiment, the deployable member does not rotate about the central axis with the rotation of the rotatable member.

Another embodiment is directed to a method, in which an electrode lead is provided. The electrode lead comprises a tubular lead body, an electrode supported by the lead body, a rotatable member, a deployable member and a deployment mechanism. The rotatable member is contained within a distal end of the tubular lead body. The deployable member is attached to the rotatable member and comprises a tissue anchor. Also in the method, the distal end of the tubular lead body is positioned proximate target tissue of a patient. The rotatable member is rotated relative to the tubular lead body. The deployable member is driven along the central axis, out the distal end of the tubular lead body, and into the target tissue using the deployment mechanism responsive to the rotation of the rotatable member. In one embodiment, the deployable member does not rotate about the central axis with the rotation of the rotatable member.

DETAILED DESCRIPTION OF ILLUSTRATIVE EMBODIMENTS

Figure 1:
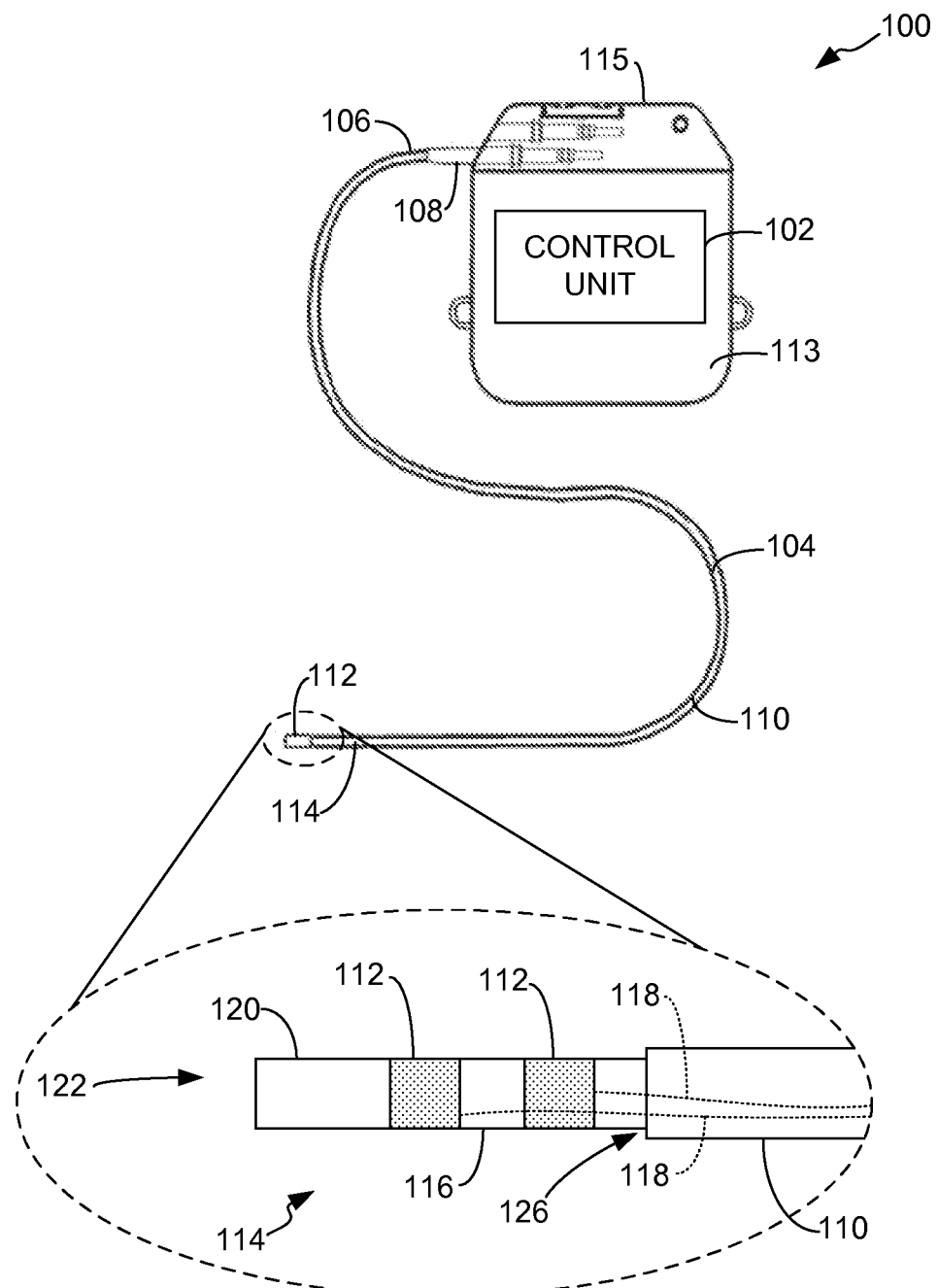
FIG. 1 is a side plan view of an exemplary electronic stimulator device, in accordance with embodiments of the invention.

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

FIG. 1 is a side plan view of an exemplary electronic stimulator device 100, in accordance with embodiments of the invention. The stimulator device 100 is configured for implantation into a pelvic region of a patient to provide muscle and/or nerve stimulation that is used to control and/or treat a pelvic condition of the patient, such as pelvic pain, urinary incontinence, fecal incontinence, erectile dysfunction or other pelvic condition that may be treated through electrical stimulation.

In one embodiment, the device 100 comprises a control unit 102 and one or more electrode leads 104, a proximal end 106 of which is electrically coupled to the control unit 102 via a connector 108. In one embodiment, the electrode lead 104 comprises a tubular lead body 110 and one or more stimulation elements or electrodes 112 supported at a distal end 114 by the lead body 110. In one embodiment, the electrodes 112 are separated from each other by an insulative portion or element 116. The lead body 110 insulates electrical wires 118 or other conductor that connects the control unit 102 to the electrodes 112. The lead body 110 can be in the form of an insulating jacket typically comprising silicone, polyurethane or other flexible, biocompatible electrically insulating material. Additional electrode leads 104 or physiological sensors may be coupled to the control unit 102.

In one embodiment, the control unit 102 comprises circuitry including at least one processor for processing electrical signals received from the one or more electrodes 112 or physiological sensors (not shown). In one embodiment, the control unit 102 is also configured to apply an electrical current or waveform to the tissue of the patient through the one or more electrodes 112 that are in contact with the tissue. In one embodiment, the control unit 102 receives power from an internal battery (not shown).

In one embodiment, the control unit 102 is enclosed within a hermetically sealed metal housing 113 commonly referred to as a "can." The can 113 generally comprises first and second halves that are joined together in a laser-welding operation about their perimeters after the battery power supply and electronic circuitry are inserted in the space defined by the two halves of the can.

A header 115 includes a connector block that may be molded in the header or inserted after the header has been molded. Feed-through conductors from the electronic circuitry within the can are coupled to electrical contacts of the connector block. The connector block includes one or more ports, each of which receives the connector 108 of each lead 104 and electrically couples the connector 108 to the electronic circuitry or control unit 102 contained within the can 113 via the feed-through conductors.

The distal end 114 of the electrode lead 104 can be anchored to pelvic tissue of the patient (e.g., urinary sphincter muscle, anal sphincter muscle, etc.) by means of a tissue anchor 120, in accordance with embodiments of the invention. Embodiments of the anchor include a helical coil, mesh and other suitable components. The anchor 120 operates to secure the position of the electrodes 112 in the desired tissue of the patient.

In one embodiment, the anchor 120 is attached to a deployable member 122 that may be deployed from within the tubular lead body, as illustrated in FIG. 1. In one embodiment, the deployable member 122 includes the one or more electrodes 112, as shown in FIG. 1.

Figure 2:
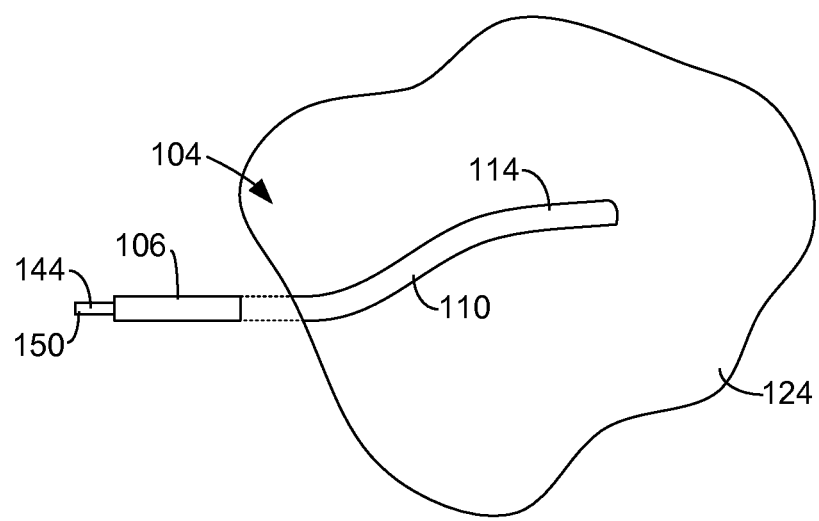
FIGS. 2 and 3 are simplified views of an electrode lead formed in accordance with embodiments of the invention positioned within tissue of a patient.

In one embodiment, the deployable member 122 has a retracted position, in which the deployable member 122 is received within the tubular lead body 110, as shown in the simplified side view of FIG. 2. While in this retracted position, the distal end 114 of the electrode lead 104 may be implanted in tissue 124 of a patient, as shown in the simplified side view of FIG. 3. The implantation of the distal end 114 of the electrode lead 104 may be accomplished using conventional techniques, such as with an introducer needle. Once the distal end 114 of the electrode lead 104 is positioned as desired within the tissue 124, the physician may use a deployment mechanism to move the deployable member 122 out an opening 126 of the tubular lead member 110, as illustrated in FIGS. 1 and 3.

Figure 3:
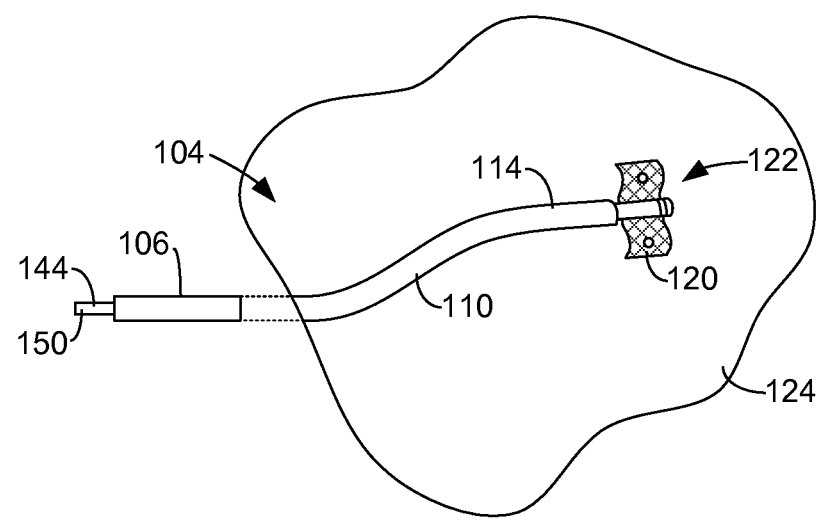
Figure 4:
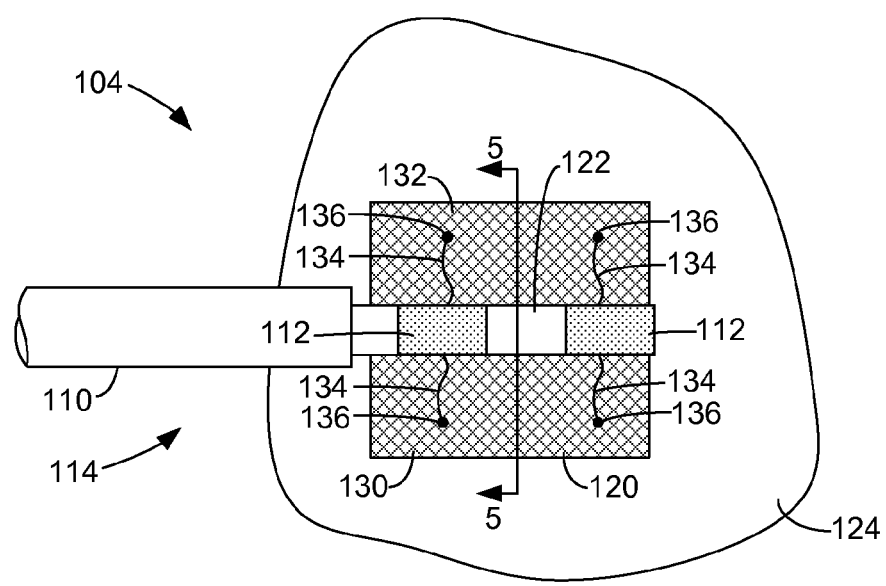
FIG. 4 is a simplified side view of a distal end of an electrode lead having a mesh anchor in a deployed position, in accordance with embodiments of the invention.
Figure 5:
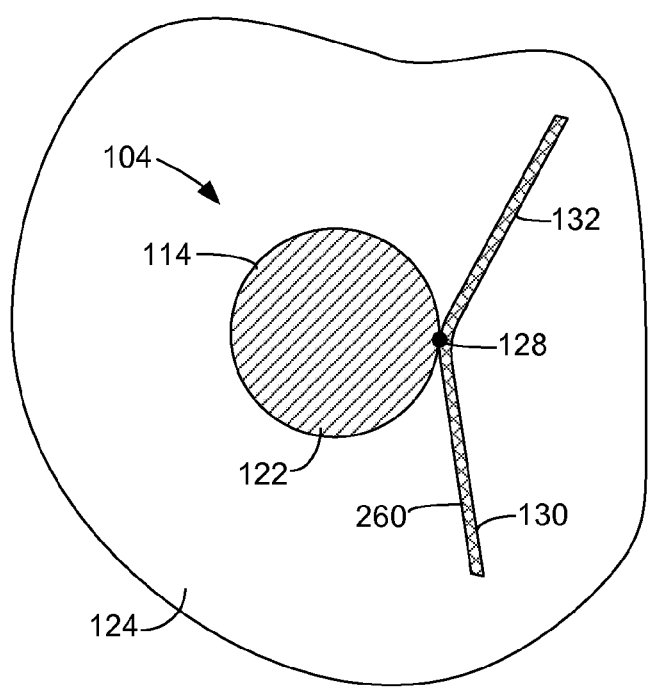
FIG. 5 is a cross-sectional view of the portion of the lead of FIG. 4 taken generally along line 5-5.

In one embodiment, the tissue anchor 120 is attached to the deployable member 122 and comprises mesh, as illustrated in FIG. 3. FIG. 4 is a simplified side view of the distal end 114 of the electrode lead 104 with the deployable member 122 having the mesh anchor 120 in the deployed position within tissue 124 of a patient. FIG. 5 is a cross-sectional view of the deployable member 122 taken generally along line 5-5 of FIG. 4 and illustrates the implantation of the distal end 114 of the electrode lead 104. In one embodiment, the mesh anchor 120 is preferably a bio-compatible open matrix mesh, such as a mesh constructed of polypropylene monofilament. A portion of the mesh anchor 120 is attached to the deployable member 122 at a location 128. Exemplary means for attaching the mesh anchor 120 to the deployable member 122 include sutures, glue, anchors, or other suitable bio-compatible methods. In one embodiment, the mesh anchor 120 comprises one or more mesh sections or wings, such as wings 130 and 132.

In one embodiment, the mesh anchor 120 has a compact state and an expanded state. The mesh anchor 120 is placed in the compact state when retracted within the tubular lead 110 (FIG. 2). When the deployable member 122 is moved through the opening 126, the mesh anchor 120 expands, as shown in FIGS. 3-5, to promote tissue ingrowth through the mesh and anchor the deployable member 122 and the distal end 114 of the electrode lead 104 in place within the tissue 124. In general, at least a portion of the mesh anchor 120 is displaced a greater distance from the deployable member 122 when in the expanded state than when in the compact state.

In one embodiment, the mesh anchor 120 has a shape memory that drives the mesh to a preset expanded, quiescent shape, in which at least a portion of the mesh anchor 120 extends away from the deployable member 122 and into the surrounding tissue 124. As used herein, the "quiescent shape" of the mesh anchor 120 is one in which the mesh will naturally return to after being deformed, such as when compressed into a compact state. In one embodiment, the expanded state of the mesh wings 130 and 132 is one in which the wings 130 and 132 are displaced from each other, such as illustrated FIG. 5. In one embodiment, a nitinol structure is secured to the mesh and promotes the expansion of the mesh. Thus, one embodiment of the mesh anchor 120 has a shape memory that encourages separation of the one or more wings, such as wings 130 and 132, within the tissue 124.

In one embodiment, the mesh anchor 120 comprises the one or more electrodes 112 that are used to deliver electrical signals to the tissue 124. In one embodiment, one or more conductive fibers 134 are attached to the mesh anchor 120 and conduct electrical signals from the deployable member 122, such as electrodes 112 on the deployable member 122, to the tissue 124, as shown in FIG. 4. In one embodiment, the conductive fibers 134 are electrically insulated from the tissue 124 and conduct the electrical signals to one or more electrically conductive nodes or electrodes 136 that are attached to the mesh anchor 120 and deliver the electrical signals to the tissue 124.

Figure 6:
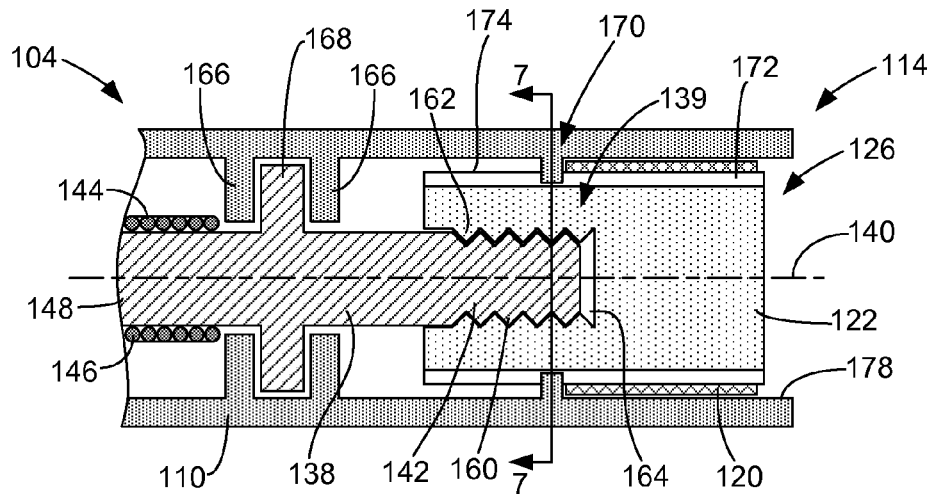
FIG. 6 is a simplified side cross-sectional view of a distal end of an electrode lead, in accordance with embodiments of the invention.
Figure 7:
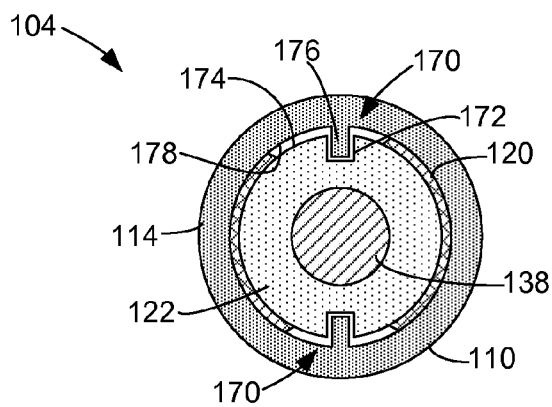
FIG. 7 is a cross-sectional view of the electrode lead of FIG. 6 taken generally along line 7-7.

FIG. 6 is a simplified side cross-sectional view of a distal end 114 of an electrode lead 104 in accordance with embodiments of the invention. FIG. 7 is a cross-sectional view of the electrode lead 104 of FIG. 6 taken generally along line 7-7. In one embodiment, the lead 104 comprises the tubular lead body 110, a rotatable member 138 within the distal end 114 of the tubular lead body 110, the deployable member 122, and a deployment mechanism 139. In one embodiment, electrode lead 104 includes one or more electrodes 112 that are supported by the lead body 110, such as through the attachment of the electrodes 112 to the lead body 110, or to the deployable member 122, for example. The electrodes 112 are not illustrated in FIG. 6 or 7 in order to simplify the drawings.

In one embodiment, the rotatable member 138 is configured to rotate about a central axis 140, which is generally aligned with the longitudinal axis of the tubular lead body 110. In one embodiment, a distal end 142 of the rotatable member 138 is attached to the deployable member 122. In one embodiment, the electrode lead 104 includes an extension member 144 having a distal end 146 that is attached to a proximal end 148 of the rotatable member 138, as shown in FIG. 6. In one embodiment, the extension member 144 has a proximal end 150 that extends to the proximal end 106 of the tubular lead body 104, as shown in FIG. 2. A physician may rotate the proximal end 150 of the extension member 144 by hand to drive the rotation of the rotatable member 138 about the central axis 140. Alternatively, a motorized device or other tool may be used to drive the rotation of the proximal end 150. In one embodiment, the extension member 144 comprises a coil, as illustrated in FIG. 6.

In one embodiment, at least one electrical conductor extends through the tubular lead body 110 and is electrically coupled to the one or more electrodes 112. In one embodiment, when the one or more electrodes 112 are disposed in or on the deployable member 122, or are otherwise electrically coupled to the deployable member 122, the rotatable member 138 is formed of or includes an electrically conductive material that conducts electrical signals to the one or more electrodes 112 through the deployable member 122. In one embodiment, the extension member 144 is used to conduct the electrical signals to the rotatable member 138. Alternatively, separate electrical conductors, such as wires 118 (FIG. 1) may extend through the lead body 110 to the rotatable member 138. Other configurations are also possible.

One embodiment of the deployment mechanism 139 is configured to drive the deployable member 122 along the central axis 140 responsive to the rotation of the rotatable member 138 about the central axis 140 to move the deployable member 122 between the retracted position (FIG. 2) and the deployed position (FIGS. 1 and 3). In one embodiment, the deployment mechanism 139 comprises a threaded section 160 of the rotatable member 138 and a threaded section 162 of the deployable member 122, as shown in FIG. 6. In one embodiment, the threaded section 160 of the rotatable member 138 is located on an exterior surface of the rotatable member 138, and the threaded section 162 is located on an interior surface of a bore 164 of the deployable member 122. However, it is understood that this arrangement may be reversed by placing the threaded section 160 of the rotatable member 138 on an interior surface of a bore, and arranging the threaded section 162 of the deployable member 122 on an exterior surface that is received within the bore of the rotatable member 138.

In one embodiment, the threaded sections 160 and 162 intermesh and the rotation of the rotatable member 138 about the central axis 140 relative to the deployable member 122 drives the deployable member 122 along the central axis 140 relative to the rotatable member 138 and the tubular lead body 110. This allows the deployable member 122 to be deployed from within the tubular lead body 110 through the opening 126, or retracted into the tubular lead body 110, through the rotation of the rotatable member 138, which is driven, for example, by the rotation of the extension portion 144.

In one embodiment, the position of the rotatable member 138 along the central axis 140 is fixed relative to the tubular lead body 110. In one embodiment, this is accomplished using one or more stop members 166 of the lead body 110 that engage a member 168 of the rotatable member 138, as shown in FIG. 6.

In one embodiment, the electrode lead 104 includes a guide 170 that is configured to prevent the deployable member 122 from rotating about the central axis 140 relative to the lead body 110. In one embodiment, the guide 170 comprises a slot 172 in an exterior wall 174 of the deployable member 122, and a protrusion 176 extending from an interior wall 178 of the lead body 110, as shown in FIGS. 6 and 7. As the deployable member 122 is moved along the central axis 140 relative to the lead body 110 responsive to the rotation of the rotatable member 138, the protrusion 176 slides within the slot 172 and prevents the deployable member 122 from rotating about the central axis 140 relative to the lead body 110. As a result, the deployable member 122 does not rotate about the central axis 140 with the rotation of the rotatable member 138. In one embodiment, the electrode lead 104 includes a pair of the guides 170, as shown in FIGS. 6 and 7. Additional guides may also be used as necessary.

Figure 8:
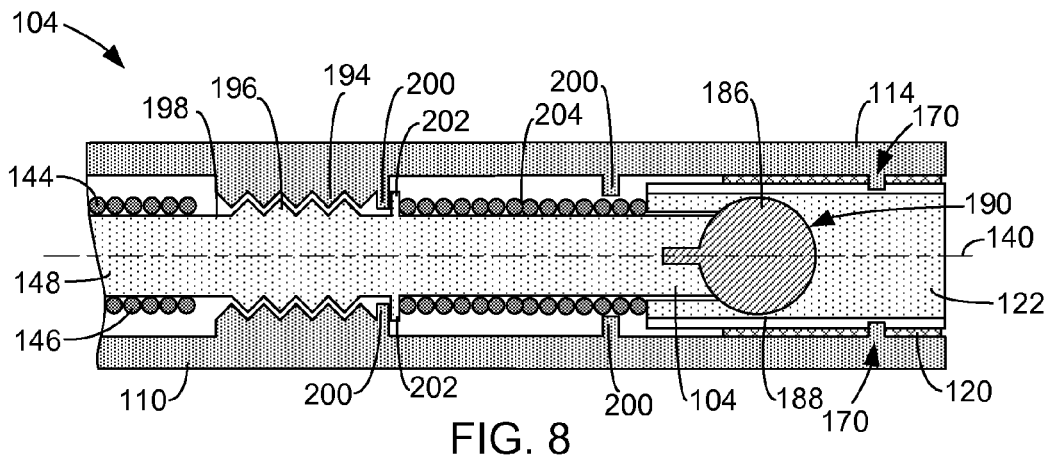
FIG. 8 is a simplified side cross-sectional view of a distal end of an electrode lead, in accordance with embodiments of the invention.

FIG. 8 is a simplified side cross-sectional view of a distal end 114 of electrode lead 104 in accordance with embodiments of the invention. In one embodiment, the deployable member 122 is coupled to the distal end 142 through a suitable mechanical connection. In one embodiment, the mechanical connection allows the deployable member 122 to remain in a fixed angular position about the central axis 140 as the rotatable member 138 rotates about the axis 140. The mechanical coupling between the deployable member 122 and the rotatable member 138 can take on many different forms while providing the desired function described above.

In one exemplary embodiment, the mechanical coupling comprises a ball member 186 coupled to the rotatable member 138, and a socket member 188 coupled to the deployable member 122. The ball member 186 is received within the socket member 188 and is able to rotate within the socket member 188. In one embodiment, a low friction interface 190 is formed between the exterior surface of the ball member 186 and the interior surface of the socket member 188. The low friction interface 190 may be formed using a suitable lubricant, an insert covering the exterior of the ball member 186, an insert covering the interior surface of the socket member 188, and/or other suitable techniques for forming a low friction interface.

In one embodiment, the deployable member 122 is restricted from rotating about the axis 140 relative to the lead body 110. In one embodiment, the lead 104 includes one or more of the guides 170 described above, as shown in FIG. 8.

Another embodiment of the deployment mechanism 139, illustrated in FIG. 8, comprises a threaded section 194 on the interior wall 178 of the tubular lead member 110, and a threaded section 196 on the exterior surface 198 of the rotatable member 138. The threaded sections 194 and 196 are positioned to intermesh with each other. Rotation of the rotatable member 138 about the axis 140 drives movement of the rotatable member 138 along the axis 140 relative to the lead body 110. Due to the mechanical coupling between the distal end 142 of the rotatable member 138 and the deployable member 122, the rotation of the rotatable member 138 about the axis 140 also drives movement of the deployable member 122 along the axis 140. Thus, the deployment mechanism 139 drives movement of the deployable member 122 along the axis 140 relative to the lead body 110 through the rotation of the rotatable member 138, and it may be used to deploy the deployable member 122 from within the lead body 110 through the opening 126 into desired tissue of a patient, and retract the deployable member 122 back into the lead body 110 through the opening 126, as described above.

In one embodiment, the movement of the rotatable member 138 along the central axis 140 is restricted by one or more stops 200 projecting from the interior wall 178 of the lead body 110 and stops 202 extending radially from the rotatable member 138. The stops 200 of the lead body 110 engage the stops 202 to limit the distance the rotatable member 138 may travel along the central axis 140 and, thus, the distance the deployable member 122 may travel along the axis 140 relative to the tubular lead member 110.

As discussed above, the deployable member 122 and/or the connected anchor 120 may include the one or more electrodes or stimulation elements 112. As discussed above, electrical signals are delivered to the one or more electrodes 112 on the deployable member 122 through an electrical conductive path that extends to the proximal end 106 of the tubular lead body 110. In one embodiment, the electrical signals are conducted to the rotatable member 138 using, for example, the extension member 144, or other suitable conductor. In one embodiment, an electrical connection is formed between the rotatable member 138 and the deployable member 122 such that electrical signals conducted to the rotatable member 138 may be delivered to the one or more electrodes 112 that are connected to the deployable member 122. In one embodiment, the electrical connection comprises a coil 204 or other suitable component that rotates about the central axis 140 with the rotation of the rotatable member 138. The coil 204 or other suitable component is placed in sliding contact with the deployable member 122 to conduct electrical signals from the rotatable member 138 to the deployable member 122. The electrical connection allows electrical signals to be delivered to the one or more electrodes 112 through the deployable member 122 while maintaining the ability to rotate the rotatable member 138 relative to the deployable member 122. In accordance with another embodiment, the electrical connection is formed between the ball member 186 and the socket member 188.

Figure 9:
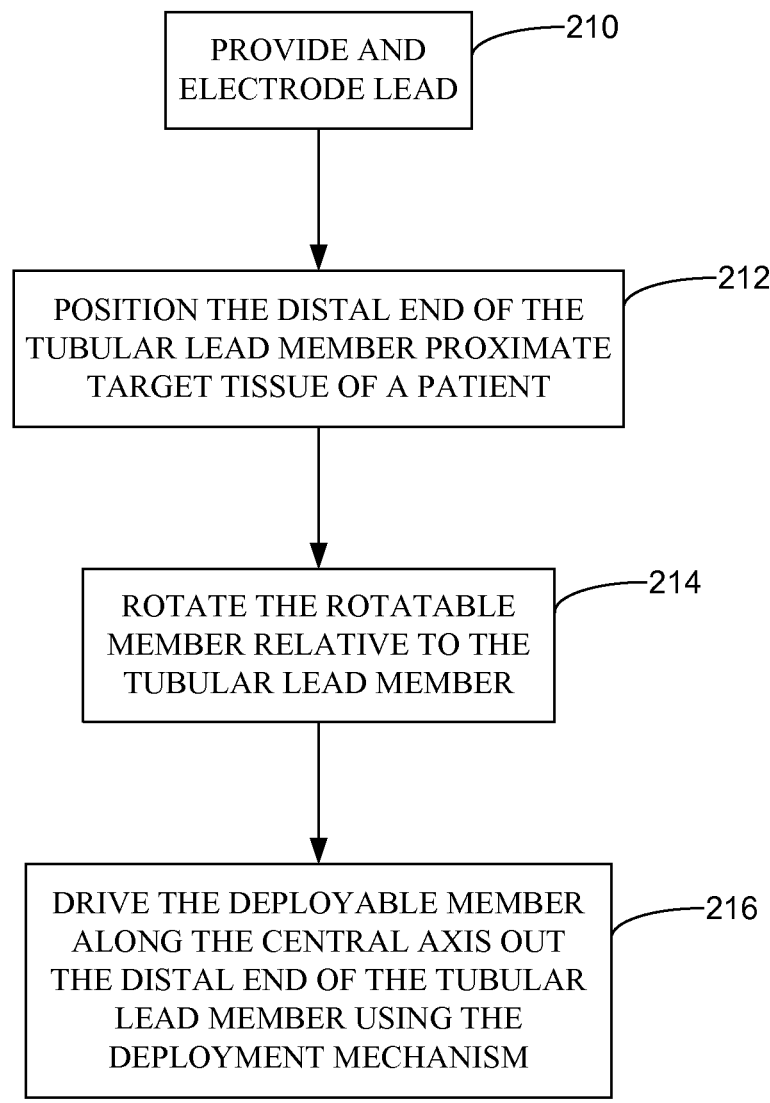
FIG. 9 is a flowchart illustrating a method of using the electrode lead formed in accordance with one or more embodiments of the invention.

FIG. 9 is a flowchart illustrating a method of using the electrode lead 104 formed in accordance with one or more embodiments described above. At 210, an electrode lead 104 formed in accordance with one or more of the embodiments described above is provided. At 212, the distal end 114 of the tubular lead member 110 is positioned approximate target tissue 124 of a patient, as shown in FIG. 2. At 214, the rotatable member 138 is rotated relative to the tubular lead member 110. As discussed above, this may be accomplished through the rotation of the proximal end 143 of the extension member 138 by the physician. At 216, the deployable member 122 is driven along the central axis 140 and out the opening 146 at the distal end 114 of the tubular lead member 110 using the deployment mechanism 139, as shown in FIG. 3.

Although the present invention has been described with reference to preferred embodiments, workers skilled in the art will recognize that changes may be made in form and detail without departing from the spirit and scope of the invention.

What is claimed is:

1. An electrode lead comprising:
   a tubular lead body;
   an electrode supported by the lead body;
   a rotatable member within a distal end of the tubular lead body;
   a deployable member attached to the rotatable member and comprising a tissue anchor, the tissue anchor comprises mesh; and
   a deployment mechanism configured to drive the deployable member along a central axis and out the distal end of the tubular lead body responsive to rotation of the rotatable member about the central axis;
   wherein the deployable member does not rotate about the central axis with the rotation of the rotatable member.

2. The electrode lead of claim 1, further comprising an extension member having a distal end attached to the rotatable member and a proximal end extending to a proximal end of the tubular lead body, wherein rotation of the extension member drives rotation of the rotatable member about the central axis.

3. The electrode lead of claim 1, wherein the deployable member includes the electrode.

4. The electrode lead of claim 3, further comprising:
   at least one electrical conductor extending within the tubular lead body from a proximal end; and
   an electrical connection between the distal end of the electrical conductor and the electrode.

5. The electrode lead of claim 4, wherein the electrical connection includes a portion that is attached to the rotatable member.

6. The electrode lead of claim 5, wherein the electrical connection rotates about the central axis responsive to rotation of the rotatable member.

7. The electrode lead of claim 1, further comprising a coupling between the rotatable member and the deployable member, the coupling configured to attach the deployable member to the rotatable member.

8. The electrode lead of claim 7, wherein the coupling comprises a ball and socket joint including a ball member attached to one of the rotatable member and the deployable member, and a socket member, which receives the ball member, attached to the other of the rotatable member and the deployable member.

9. The electrode lead of claim 7, wherein the deployment mechanism comprises:
   a first threaded section attached to the rotatable member; and
   a second threaded section attached to the deployable member that intermeshes with the first threaded section;
   wherein the rotation of the rotatable member about the central axis relative to the deployable member drives the deployable member along the central axis relative to the tubular lead body due to the intermeshing of the first and second threaded sections.

10. The electrode lead of claim 1, wherein the deployment mechanism comprises:
    a first threaded section on an interior wall of the tubular lead body; and
    a second threaded section on an exterior wall of the rotatable member that intermeshes with the first threaded section;
    wherein rotation of the rotatable member about the central axis drives the rotatable member along the central axis due to the intermeshing of the first and second threaded sections.

11. The electrode lead of claim 1, further comprising at least one stop member that limits movement of at least one of the rotatable member and the deployable member along the central axis.

12. The electrode lead of claim 1, further comprising a guide configured to prevent the deployable member from rotating about the central axis.

13. The electrode lead of claim 12, wherein the guide comprises a slot in an exterior wall of the deployable member, and a protrusion extending from an interior wall of the tubular lead body that is received within the slot.

* * * * *